United States Patent
Yang et al.

(10) Patent No.: US 11,918,214 B2
(45) Date of Patent: Mar. 5, 2024

(54) SHIPPING WEDGE FOR STAPLE CARTRIDGE

(71) Applicant: Covidien LP, Mansfield, MA (US)

(72) Inventors: Qianhong Yang, Shanghai (CN); Hui Zhan, Shanghai (CN)

(73) Assignee: Covidien LP, Mansfield, MA (US)

( * ) Notice: Subject to any disclaimer, the term of this patent is extended or adjusted under 35 U.S.C. 154(b) by 218 days.

(21) Appl. No.: 17/310,045

(22) PCT Filed: Feb. 11, 2019

(86) PCT No.: PCT/CN2019/074793
§ 371 (c)(1),
(2) Date: Jul. 13, 2021

(87) PCT Pub. No.: WO2020/163982
PCT Pub. Date: Aug. 20, 2020

(65) Prior Publication Data
US 2022/0047264 A1 Feb. 17, 2022

(51) Int. Cl.
*A61B 17/072* (2006.01)
*A61B 17/068* (2006.01)
*A61B 90/00* (2016.01)

(52) U.S. Cl.
CPC .... *A61B 17/07207* (2013.01); *A61B 17/0686* (2013.01); *A61B 90/03* (2016.02);
(Continued)

(58) Field of Classification Search
CPC ............ A61B 17/0684; A61B 17/0686; A61B 17/0688; A61B 17/07207; A61B 17/285;
(Continued)

(56) References Cited

U.S. PATENT DOCUMENTS

2005/0222616 A1 10/2005 Rethy et al.
2013/0062391 A1* 3/2013 Boudreaux ...... A61B 17/07292
227/175.1
(Continued)

FOREIGN PATENT DOCUMENTS

CN 102048568 A 5/2011
CN 104027141 A 9/2014
(Continued)

OTHER PUBLICATIONS

International Search Report dated Nov. 14, 2019, issued in corresponding international appln No. PCT/CN2019/074793, 13 pages.

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

A shipping wedge (10) for a staple cartridge includes a body (12), an elongate fin (22), at least one tooth (32), and a knife stop (20). The elongate fin (22) is supported on a bottom surface (16) of the body (12). The tooth (32) extends from the bottom surface (16) on the proximal portion of the body (12) and is positioned to be received within a recess formed in the staple cartridge (102). The knife stop (20) extends from a top surface (14) of the proximal end of the body and is positioned to obstruct movement of a knife bar (122) of the staple cartridge (102) when the shipping wedge (10) is attached to the staple cartridge (102). A sled stop member (26) extends from the bottom surface (16) on the proximal portion of the body (12) of the shipping wedge (10) and is positioned to obstruct movement of an actuation sled of the staple cartridge (102).

16 Claims, 8 Drawing Sheets

(52) U.S. Cl.
CPC ............... *A61B 2017/07271* (2013.01); *A61B 2017/07278* (2013.01); *A61B 2017/07285* (2013.01); *A61B 2090/038* (2016.02)

(58) Field of Classification Search
CPC ........ A61B 17/295; A61B 2017/07271; A61B 2017/07278; A61B 2017/07285; A61B 2017/07214–0725; A61B 2017/0053; A61B 17/105; A61B 50/30; A61B 2050/0059; A61B 2050/005
USPC ........................................... 227/175.1–182.1
See application file for complete search history.

(56) References Cited

U.S. PATENT DOCUMENTS

| | | | |
|---|---|---|---|
| 2014/0183244 A1* | 7/2014 | Duque | A61B 17/068 606/167 |
| 2014/0252065 A1* | 9/2014 | Hessler | A61B 17/07207 227/176.1 |
| 2016/0249929 A1* | 9/2016 | Cappola | A61B 17/068 227/176.1 |
| 2022/0079596 A1* | 3/2022 | Huitema | A61B 17/0644 |

FOREIGN PATENT DOCUMENTS

| | | |
|---|---|---|
| CN | 105748125 A | 7/2016 |
| EP | 2308390 A1 | 4/2011 |

* cited by examiner

SHIPPING WEDGE FOR STAPLE CARTRIDGE

BACKGROUND

1. Technical Description

The present disclosure is directed to a shipping wedge for a staple cartridge of a surgical stapling device and, more particularly, to a shipping wedge for a staple cartridge of a linear surgical stapling device for preventing advancement of a knife bar and for retaining staples within the staple cartridge.

2. Background of Related Art

Surgical stapling devices that include replaceable staple cartridges are commonly used in surgical procedures for joining tissue segments. Typically, the staple cartridge includes a body that defines a central knife slot and includes a knife bar having a cutting edge. The shipping wedge includes an elongated fin that is received within the knife slot of the staple cartridge to frictionally secure the shipping wedge to the staple cartridge in a position to prevent advancement of a knife bar.

In known shipping wedges, the elongated fin includes small ribs that increase the frictional resistance between the elongated fin and the body of the staple cartridge to retain the shipping wedge in a desired position in relation to the staple cartridge to prevent advancement of the knife bar during shipping and storage. However, the frictional resistance of the elongated fin and the ribs may not be sufficient retain the shipping wedge in the desired position on the staple cartridge.

A continuing need exists in the art for an improved shipping wedge that can prevent movement of the knife bar and retain staples within the body of the staple cartridge.

SUMMARY

One aspect of the present disclosure is directed to a shipping wedge for a staple cartridge that includes a body, an elongate fin, at least one tooth, and a knife stop. The body has a top surface, a bottom surface, a distal portion and a proximal portion. The elongate fin is supported on the bottom surface of the body and is configured and dimensioned to be received within a knife bar slot of a staple cartridge. The at least one tooth extends from the bottom surface on the proximal portion of the body and is positioned to be received within recesses formed in the staple cartridge to prevent longitudinal movement of the shipping wedge in relation to the staple cartridge. The knife stop extends from the top surface of the proximal end of the body and is positioned to obstruct movement of the knife bar of the staple cartridge when the shipping wedge is attached to the staple cartridge.

Another aspect of the present disclosure is directed to a shipping wedge and staple cartridge assembly that includes a shipping wedge and a staple cartridge. The staple cartridge has a body defining a central knife bar slot and plurality of staple retention slots positioned on each side of the knife bar slot. Each of the staple retention slots supports a staple. The staple cartridge has a knife bar and an actuation sled. The knife bar is movable through the knife bar slot from a retracted position to an advanced position to advance the sled and eject staples from the staple cartridge. The body of the staple cartridge has a distal portion defining at least one recess. The shipping wedge has a body, an elongate fin, at least one tooth, and a knife stop. The body of the shipping wedge includes a top surface, a bottom surface, a distal portion and a proximal portion. The elongate fin is supported on the bottom surface of the body and is configured and dimensioned to be received within the knife bar slot of the staple cartridge to secure the shipping wedge to the staple cartridge. The at least one tooth extends from the bottom surface on the proximal portion of the body of the shipping wedge and is positioned to be received within the at least one recess of the staple cartridge to prevent longitudinal movement of the shipping wedge in relation to the staple cartridge. The knife stop extends from the top surface of the proximal end of the body and is positioned to obstruct movement of the knife bar of the staple cartridge when the shipping wedge is attached to the staple cartridge.

In embodiments, a sled stop member extends from the bottom surface on the proximal portion of the body of the shipping wedge.

In some embodiments, the sled stop member includes an angled stop surface.

In certain embodiments, the angle of the angled stop surface is selected to correspond to an angle of a distal portion of the actuation sled of the staple cartridge.

In embodiments, the elongate fin includes one or more ribs that are dimensioned to increase frictional resistance between the fin and the staple cartridge.

In some embodiments, the knife stop includes a base member and a stop surface supported on the base member.

In certain embodiments, the stop member has a width that is greater than the width of the base member.

In embodiments, the base member has a triangular configuration with an apex spaced from the top surface of the body, wherein the stop member is supported on the base member adjacent the apex.

In some embodiments, gripping members extend transversely outwardly of the body of the shipping wedge.

In certain embodiments, the at least one tooth includes a tooth positioned on each side of the elongated fin.

In embodiments, the body defines a transverse axis and a longitudinal axis and the body has a stepped configuration along the transverse axis.

In some embodiments, the bottom surface of the body has a stepped configuration along the transverse axis.

BRIEF DESCRIPTION OF THE DRAWINGS

Various embodiments of the presently disclosed shipping wedge are described herein below with reference to the drawings, wherein.

DETAILED DESCRIPTION OF EMBODIMENTS

Figure 1:
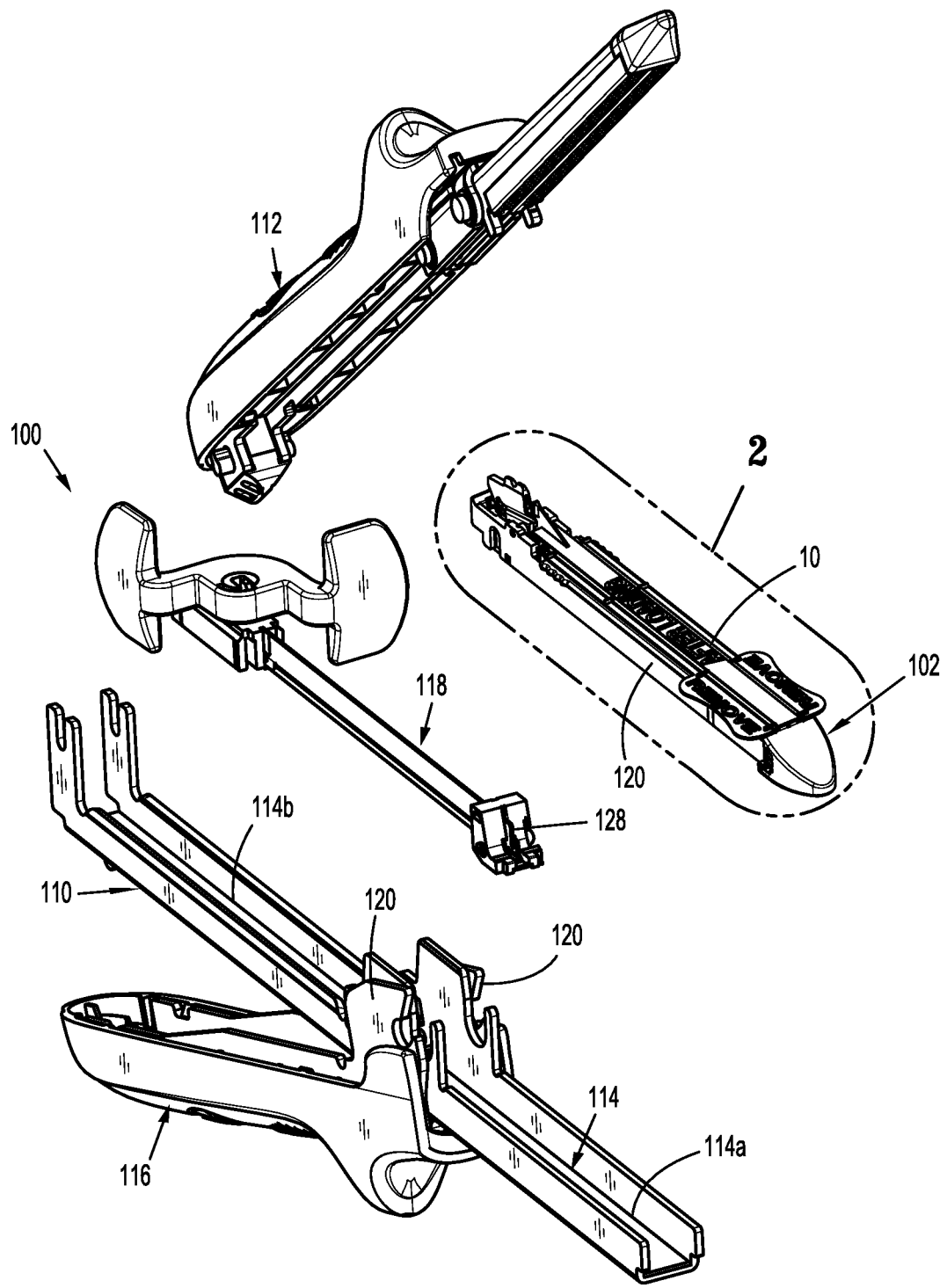
FIG. 1 is a side perspective view of a surgical stapling device including a staple cartridge with an exemplary embodiment of the presently disclosed shipping wedge secured to the staple cartridge.

The presently disclosed shipping wedge will now be described in detail with reference to the drawings in which like reference numerals designate identical or corresponding elements in each of the several views. It is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Referring to FIG. 1, the presently disclosed staple cartridge shipping wedge is shown generally as shipping wedge 10. The shipping wedge 10 is received on a staple cartridge 102 of a linear stapling device 100. The linear stapling device 100 includes cartridge receiving half-section 110, an anvil half-section 112, a clamp lever 116, and a firing assembly 118. The cartridge receiving half-section 110 defines a channel 114 that has a distal portion 114a that receives the staple cartridge 102 and a proximal portion 114b that receives the firing assembly 118. The clamp lever 116 is secured to the cartridge receiving half-section 110 and includes flange portions 120 that are movable into engagement with the anvil receiving half-section 112 to move the anvil receiving half-section 112 to a clamped position in relation to the cartridge receiving half section 110.

Figure 2:
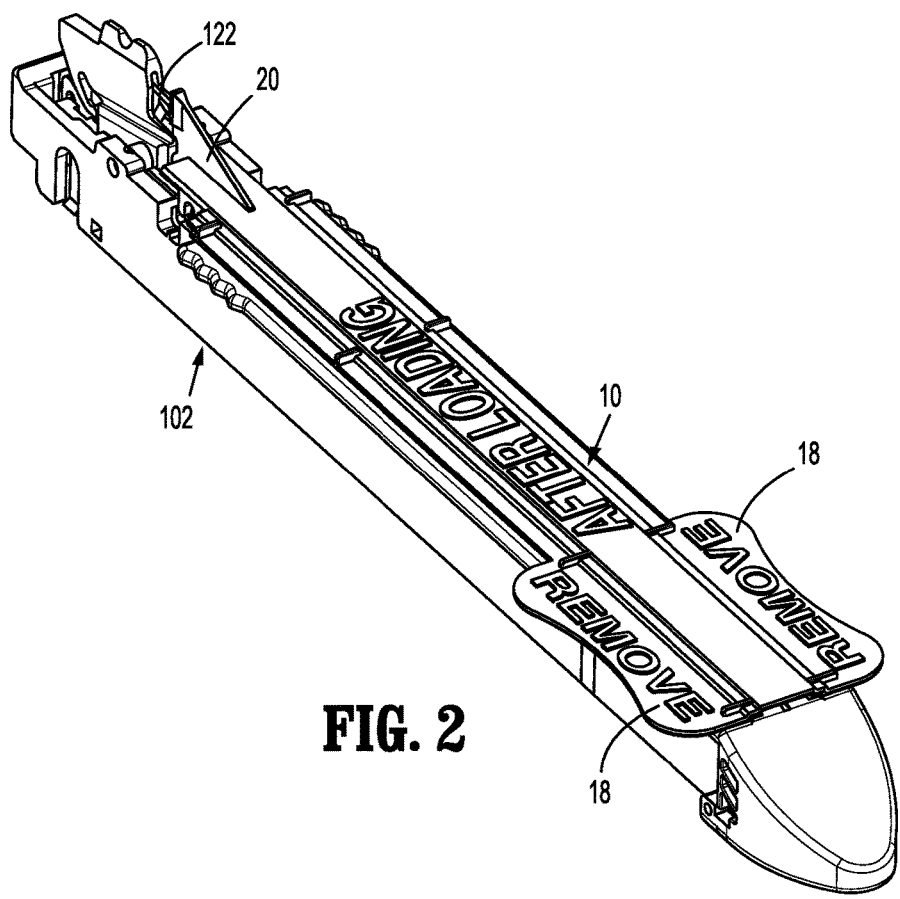
FIG. 2 is an enlarged view of the indicated area of detail shown in FIG. 1.
Figure 3:
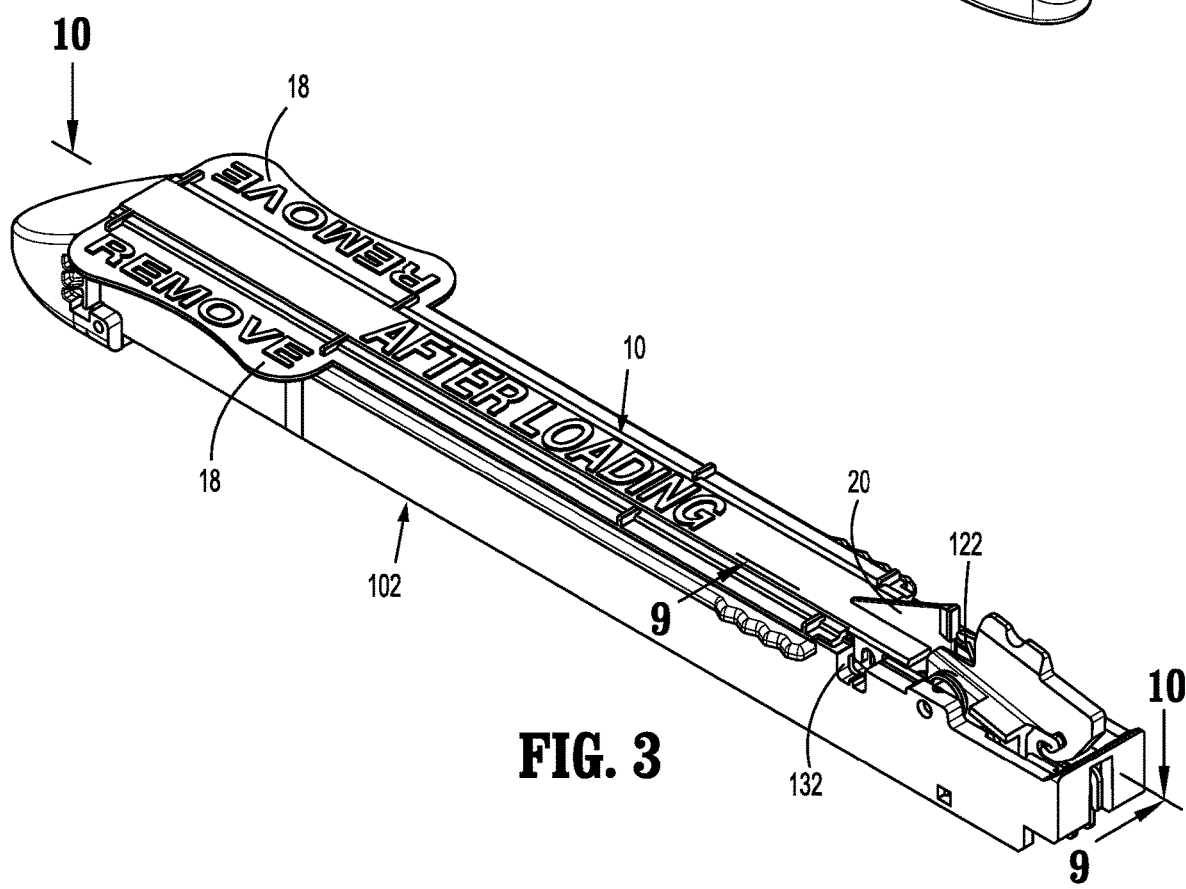
FIG. 3 is a side perspective view of the staple cartridge and shipping wedge shown in FIG. 2 from the proximal end of the staple cartridge.
Figure 4:
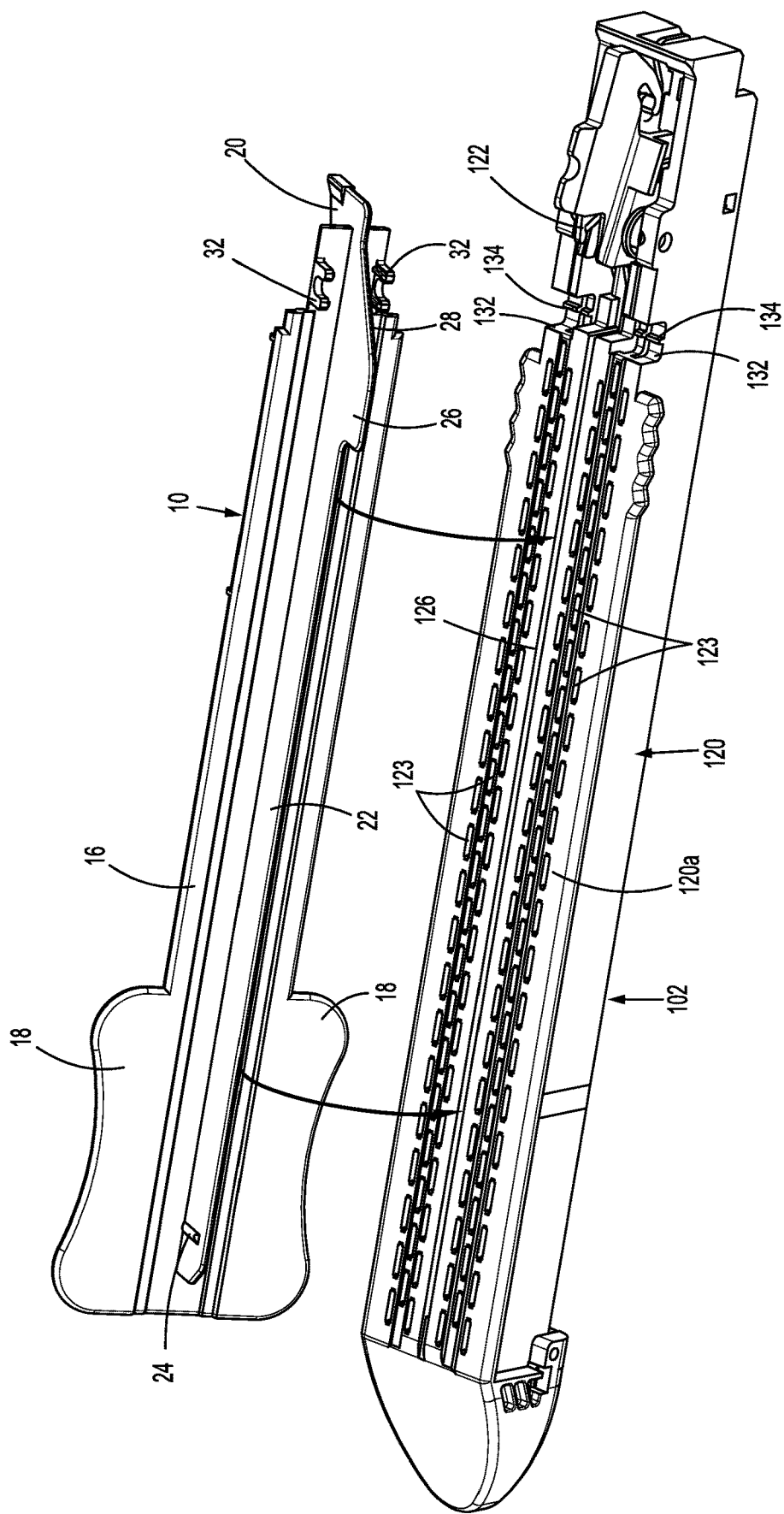
FIG. 4 is a side perspective view of the staple cartridge and shipping wedge shown in FIG. 3 with the shipping wedge separated from the staple cartridge.
Figure 12:
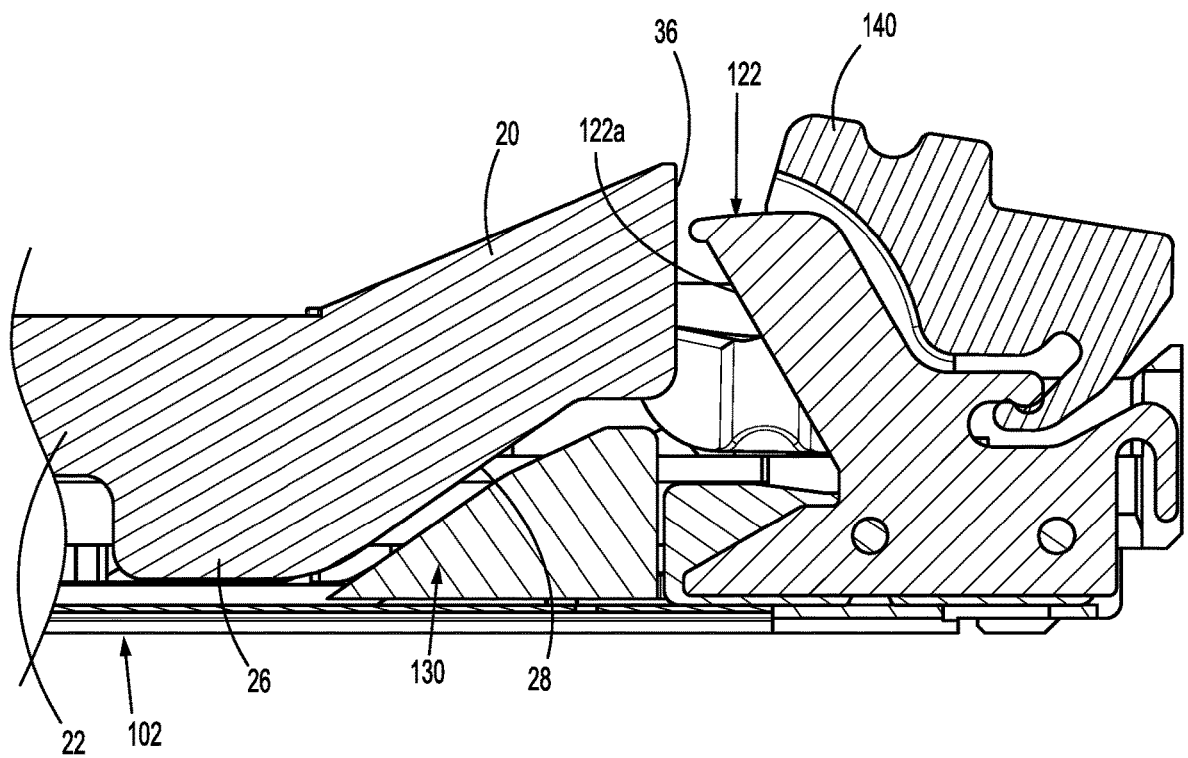
FIG. 12 is a cross-sectional view taken along section line 12-12 of FIG. 10.
Figure 13:
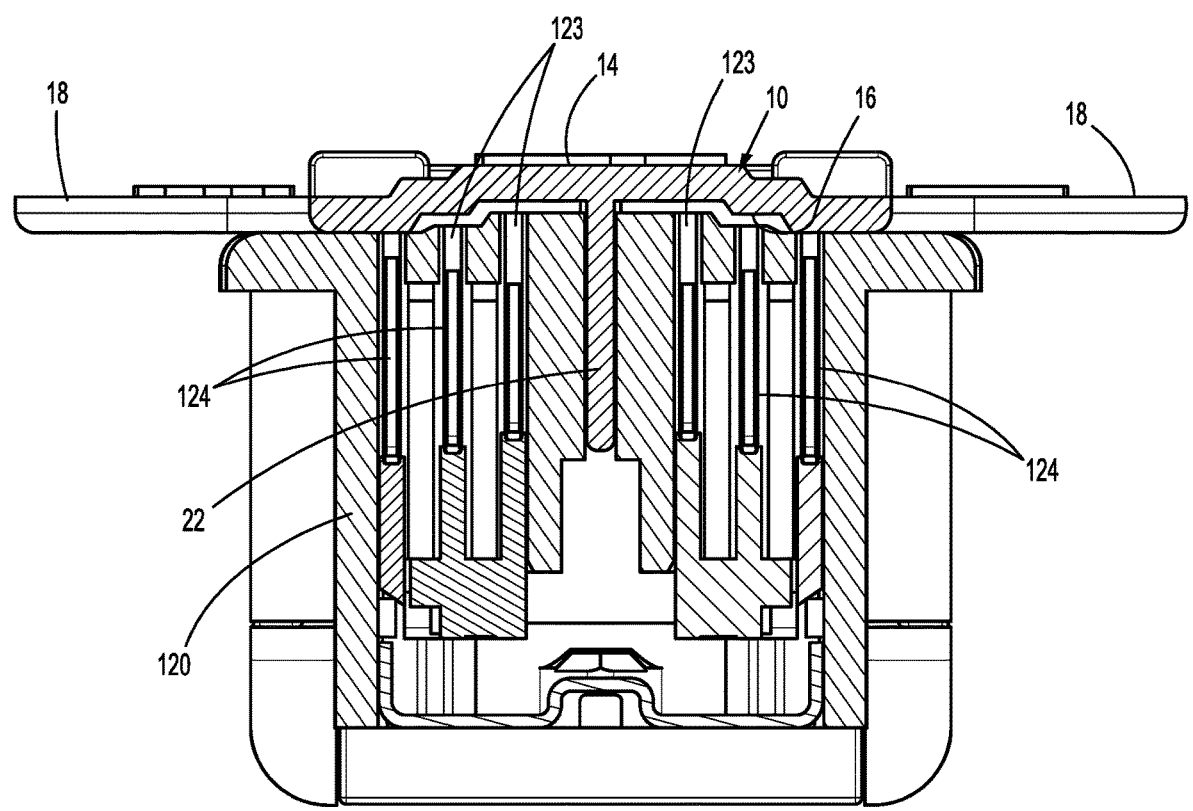
FIG. 13 is a cross-sectional view taken along section line 13-13 of FIG. 10.

Referring also to FIGS. 2-4, the staple cartridge 102 includes a body 120 and a knife bar 122 having a cutting blade 122a (FIG. 9) that is movable within the body 120 of the staple cartridge 102. The body 120 of the staple cartridge 102 has a tissue contact surface 120a (FIG. 4) that defines a plurality of rows of retention slots 123 that receive staples 124 (FIG. 13) and a central knife bar slot 126 (FIG. 4). The firing assembly 118 includes a drive member 128 (FIG. 1) that is adapted to be coupled to the knife bar 122 when the staple cartridge 102 is positioned within the distal portion 114a of the channel 114 such that longitudinal movement of the drive member 128 causes corresponding longitudinal movement of the knife bar 122 within the staple cartridge 102. The staple cartridge 102 also includes an actuation sled 130 (FIG. 12) that is engaged by the knife bar 122 and advanced within the staple cartridge 102 to eject the staples 124 from the staple cartridge 102. For a detailed description of an exemplary surgical stapling device see, e.g., U.S. Pat. Nos. 7,721,933 and 7,055,730 and U.S. Publication Number 2016/0262756 which are incorporated herein by reference in their entirety.

Figure 11:
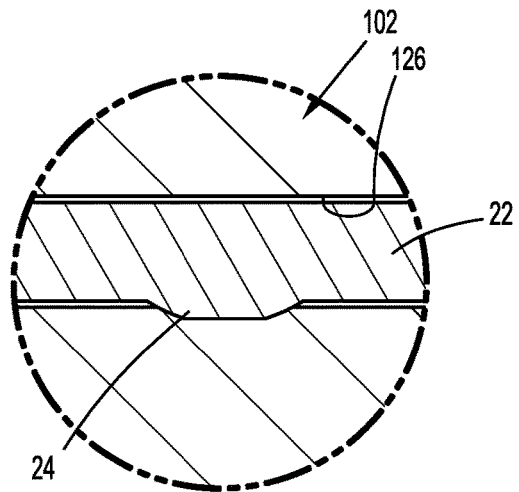
FIG. 11 is an enlarged view of the indicated area of detail shown in FIG. 10.

Referring to FIGS. 2-8, the shipping wedge 10 includes a body 12 having a proximal portion and a distal portion. The body 12 includes a top surface 14, a bottom surface 16, gripping tabs 18, a knife stop 20 positioned on the proximal portion of the body 12, and an elongated fin 22 extending downwardly from the bottom surface of the body 12. The elongated fin 22 extends a substantial portion of the length of the body 12 and is dimensioned to be frictionally received and retained within the knife bar slot 126 (FIG. 4) defined in the body 120 of the staple cartridge 102. In embodiments, the elongated fin 22 includes one or more ribs or raised surfaces 24 (FIG. 11) that are received within the knife bar slot 126 of the staple cartridge 102 to increase resistance between the staple cartridge 102 and the elongated fin 22 and obstruct removal of the shipping wedge from the staple cartridge 102.

The elongated fin 22 of the shipping wedge 10 includes a sled stop member 26 (FIG. 5) that has a proximal portion that defines an angled stop surface 28. When the elongated fin 22 is received within the knife bar slot 126 of the staple cartridge 102, the angled stop surface 28 of the sled stop member 26 is positioned adjacent the actuation sled 130 (FIG. 12) to prevent any substantial distal advancement of the actuation sled 130 within the staple cartridge 102. In embodiments, the angled stop surface 28 of the sled stop member 26 defines an acute angle that corresponds to the angle of the distal portion of the actuation sled 130 although other configurations are envisioned.

The proximal portion of the body 12 of the shipping wedge 10 includes projections or teeth 32 (FIG. 4) that extend downwardly from the bottom surface 16 of the body 12 of the shipping wedge 10 on each side of the elongated fin 22. The teeth 32 are received within recesses 132 formed in the proximal portion of the body 120 of the staple cartridge 102. In embodiments, slots 134 may defined within the recesses 132 that receive the teeth 32 to more securely fix the shipping wedge 10 to the staple cartridge 102.

Figure 9:
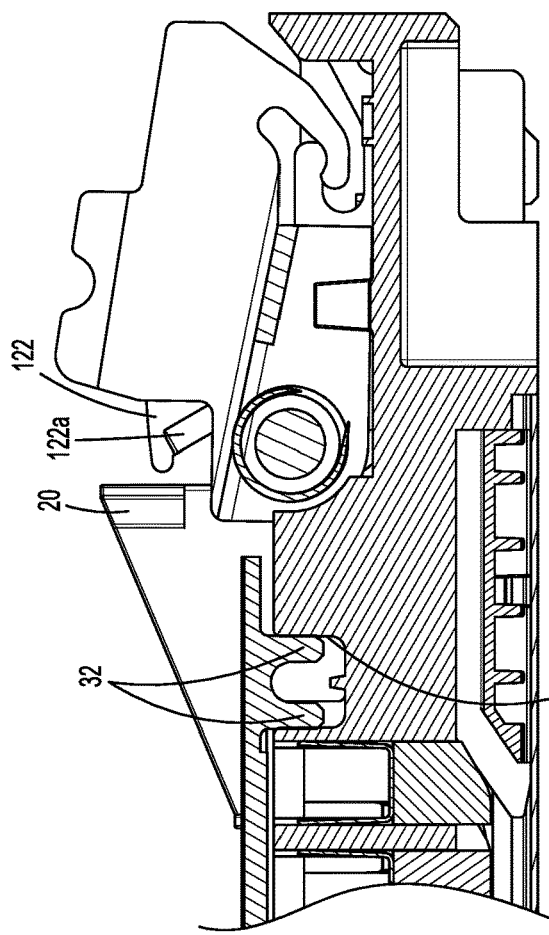
FIG. 9 is a cross-sectional view taken along section line 9-9 of FIG. 3.
Figure 10:
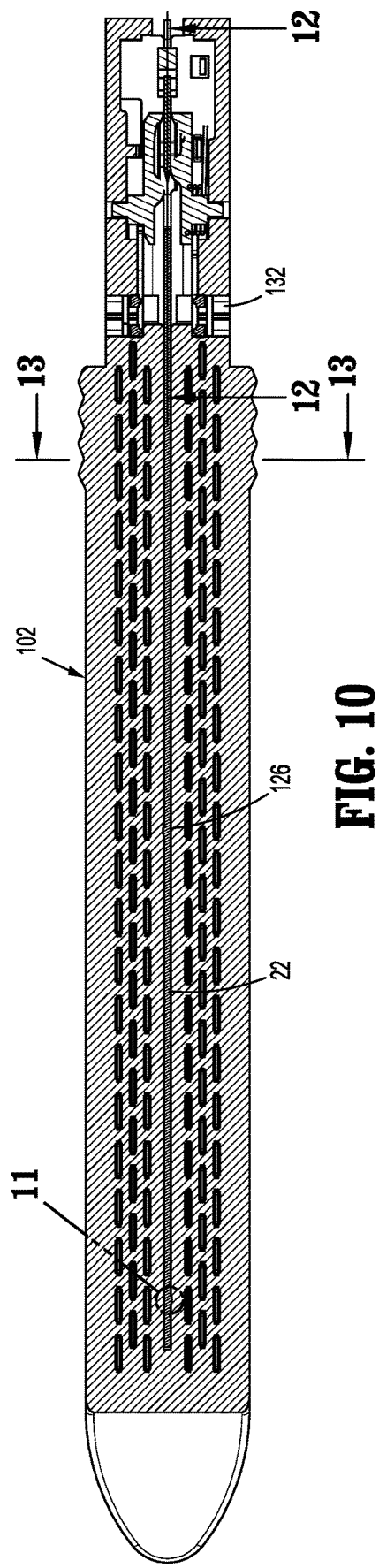
FIG. 10 is a cross-sectional view taken along section line 10-10 of FIG. 3.

The distal portion of the body 12 of the shipping wedge 10 supports the knife stop 20. The knife stop 20 extends upwardly from the top surface 14 (FIG. 5) of the body 12 of the shipping wedge 10. The knife stop 20 includes a base member 34 and a stop surface 36 that is positioned to engage a distal end of the knife bar 122 (FIG. 9). In embodiments, the stop surface 36 of the knife stop 20 has a width that is greater than the width of the base member 34 and is positioned at a height that is the same or greater than the height of the knife bar 122. In some embodiments, the base member 34 has a triangular configuration and the stop member 36 is positioned adjacent the apex of the base member 34 at a location spaced from the top surface 14 of the body 12 of the shipping wedge 10.

Figure 5:
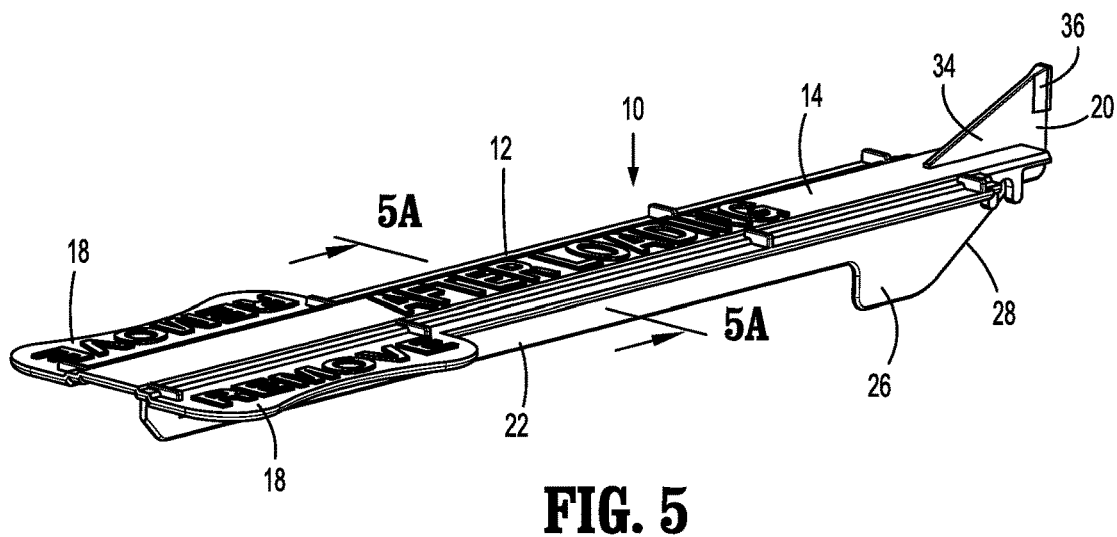
FIG. 5 is a side perspective view from above of the shipping wedge shown in FIG. 4.
Figure 5A:
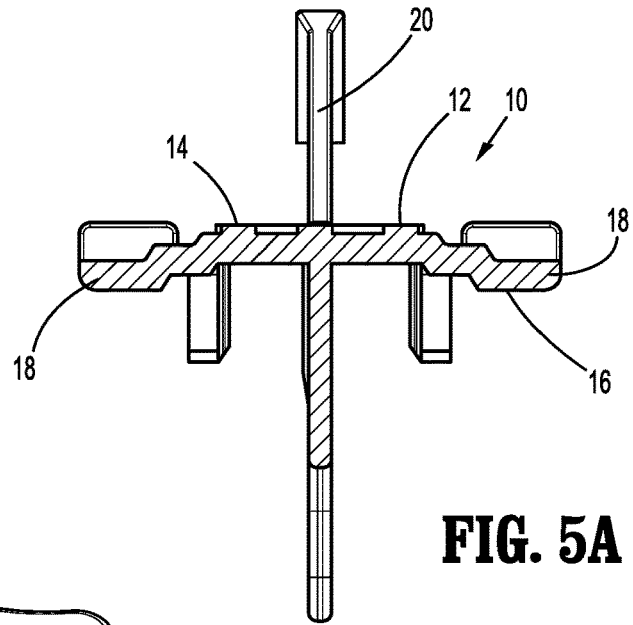
FIG. 5A is a cross-sectional view along section line 5-5 of FIG. 5.
Figure 6:
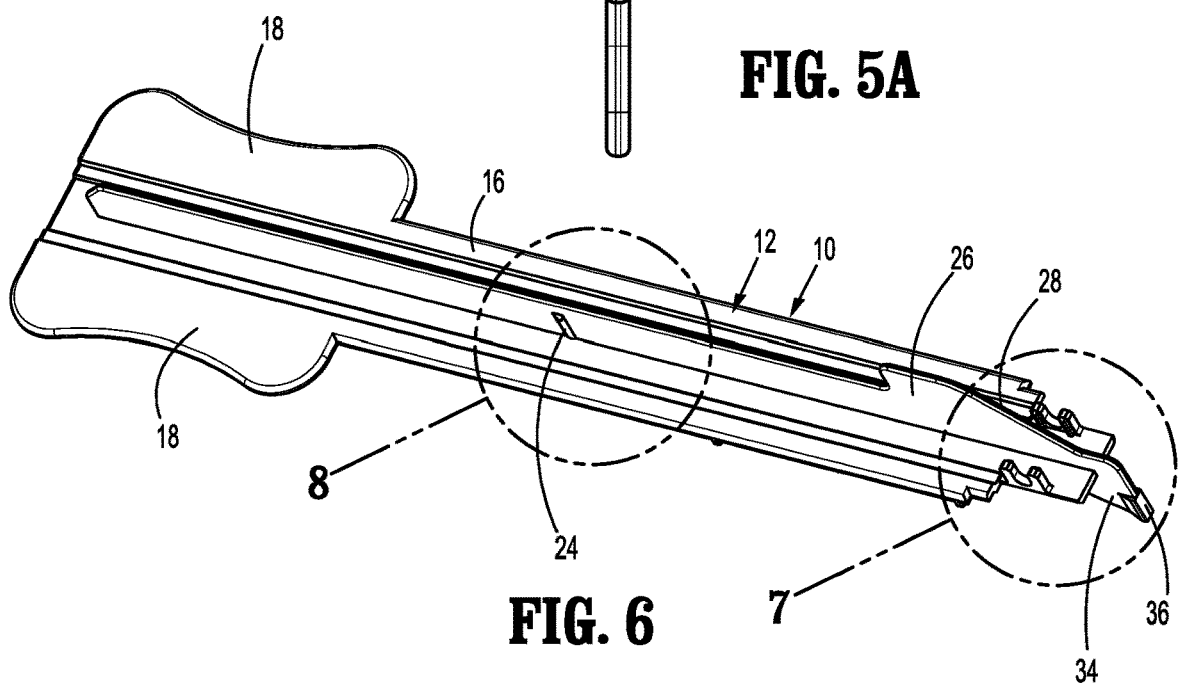
FIG. 6 is a side perspective view from below of the shipping wedge shown in FIG. 5.
Figure 7:
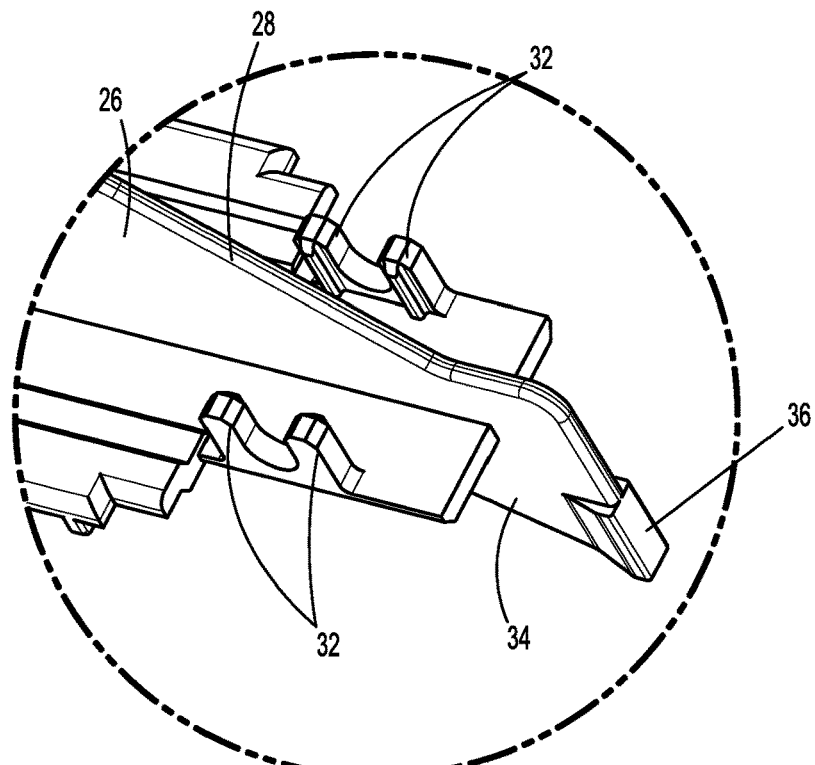
FIG. 7 is an enlarged view of the indicated area of detail shown in FIG. 6.
Figure 8:
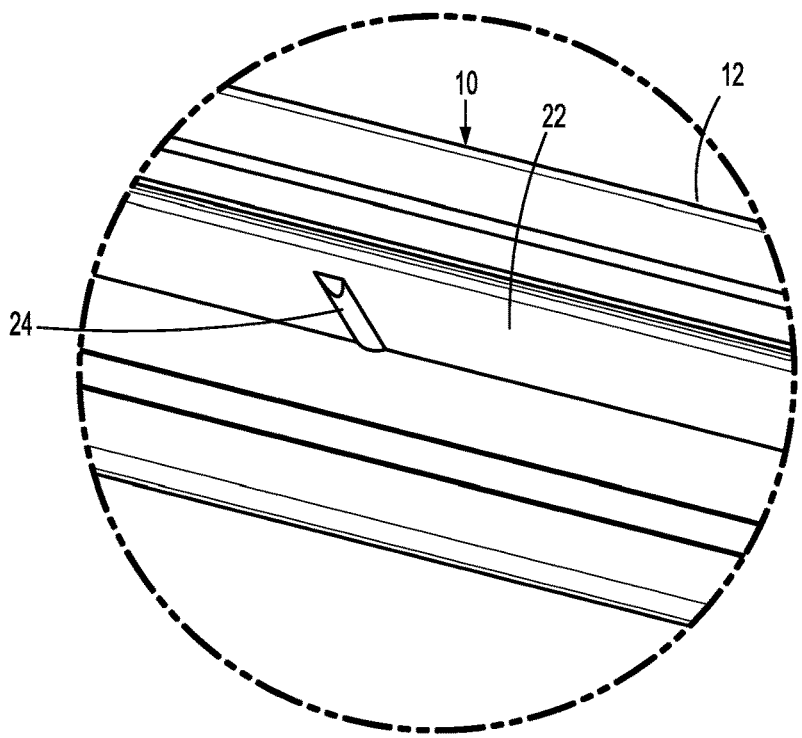
FIG. 8 is an enlarged view of the indicated area of detail shown in FIG. 6.

Referring to FIG. 5A, in embodiments, the top and/or bottom surfaces 14, 16, respectively, of the body 12 of the shipping wedge 10 may have a stepped configuration to conform to the configuration of a staple cartridge. In embodiments, the bottom surface 16 of the body 12 of the shipping wedge 10 is stepped to correspond to the stepped tissue contact surface 120a of the staple cartridge 102. The stepped configuration of the body 12 of the shipping wedge 10 allows the shipping wedge to be in closer approximation with the tissue contact surface 120a of the staple cartridge 102 to reduce the degree to which tips of the staples 124 (FIG. 13) can protrude outwardly of the retention slots 123 in the staple cartridge 102.

Referring to FIGS. 9-13, when the shipping wedge is secured to the staple cartridge 102 (FIG. 2), the elongated fin 22 is positioned within the knife bar slot 126 (FIG. 10) of the staple cartridge 102 such that the teeth 32 (FIG. 9) of the shipping wedge 10 are received within the recesses 132 of the staple cartridge 102. This longitudinally and transversely aligns the shipping wedge 100 with the staple cartridge 102. In this position, the stop surface 36 of the knife stop 20 is positioned distally of the knife bar 122 (FIG. 12) of the staple cartridge 102 to prevent any substantial advancement of the knife bar 122 within the staple cartridge 102. Similarly, in this position, the sled stop member 26 is positioned distally of the actuation sled 130 such that the angled stop surface 28 of the sled stop member 26 is positioned to prevent any substantial advancement of the actuation sled 130 within the staple cartridge 102. As discussed above, the combination of the elongated fin 22 and the teeth 32 prevent movement of the shipping wedge 10 in relation to the staple cartridge 102 to maintain the knife bar 122 in a safe position within a guard 140 (FIG. 12) of the staple cartridge 102.

Although the shipping wedge 10 is shown as being integrally formed as a monolithic structure, it is envisioned that the shipping wedge 10 can be formed of multiple components that are attached together. For example, any one or all of the knife stop 20, the elongated fin 22, the sled stop member 26, and the teeth 32 can be independently formed and secured to the body 12 of the shipping wedge using any known fastening technique including welding, over molding, or the like. Alternatively, it is envisioned that the shipping wedge 10 can integrally formed by molding from a single material.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A shipping wedge for a staple cartridge comprising:
   a body defining a central longitudinal axis and having a top surface, a bottom surface, a distal portion, and a proximal portion;
   an elongate fin supported on the bottom surface of the body, the elongate fin extending along the central longitudinal axis and configured and dimensioned to be received within a knife bar slot of a staple cartridge;
   teeth extending from the bottom surface of the proximal portion of the body, one of the teeth positioned on each side of the elongate fin entirely outwardly of the central longitudinal axis with the elongate fin positioned between the teeth, the teeth positioned to be received within recesses formed in the staple cartridge to prevent longitudinal movement of the shipping wedge in relation to the staple cartridge; and
   a knife stop extending from the top surface of the proximal portion of the body, the knife stop being positioned to obstruct movement of a knife bar of the staple cartridge when the shipping wedge is attached to the staple cartridge.

2. The shipping wedge of claim 1, further including a sled stop member extending from the bottom surface on the proximal portion of the body.

3. The shipping wedge of claim 2, wherein the sled stop member includes a stop surface that defines an acute angle with the longitudinal axis of the body of the shipping wedge.

4. The shipping wedge of claim 3, wherein the angle of the angled stop surface is selected to correspond to an angle of a distal portion of an actuation sled of the staple cartridge.

5. The shipping wedge of claim 1, wherein the elongate fin includes one or more ribs that are dimensioned to increase frictional resistance between the fin and the staple cartridge.

6. The shipping wedge of claim 1, wherein the knife stop includes a base member and a stop surface supported on the base member.

7. The shipping wedge of claim 6, wherein the stop surface has a width that is greater than the width of the base member.

8. The shipping wedge of claim 7, wherein the base member has a triangular configuration with an apex spaced from the top surface of the body, the stop surface being supported on the base member adjacent the apex.

9. The shipping wedge of claim 1, further including gripping members extending transversely outwardly of the body.

10. The shipping wedge of claim 1, wherein the body defines a transverse axis and a longitudinal axis, the body having a stepped configuration along the transverse axis.

11. The shipping wedge of claim 1, wherein the body defines a transverse axis and a longitudinal axis, the bottom surface of the body having a stepped configuration along the transverse axis.

12. A shipping wedge and staple cartridge assembly comprising:
   a staple cartridge having a body defining a longitudinal axis, a central knife bar slot and a plurality of staple retention slots positioned on each side of the knife bar slot, each of the staple retention slots supporting a staple, the staple cartridge having a knife bar and an actuation sled, the actuation sled having an angled distal portion configured to eject the staples from the body of the staple cartridge, the knife bar being movable through the knife bar slot from a bar retracted position to a bar advanced position to advance the sled from a sled retracted position to a sled advanced position and eject staples from the staple cartridge, the body of the staple cartridge having a proximal portion defining at least one recess; and
   a shipping wedge having a body including a top surface, a bottom surface extending along the longitudinal axis, a distal portion, a proximal portion, an elongate fin, at least one tooth, a knife stop, and a sled stop member, the elongate fin supported on the bottom surface of the body of the shipping wedge and configured and dimensioned to be received within the knife bar slot of the staple cartridge to secure the shipping wedge to the staple cartridge, the at least one tooth extending from the bottom surface of the proximal portion of the body of the shipping wedge and positioned outwardly of the elongate fin, the at least one tooth received within the at least one recess of the staple cartridge to prevent longitudinal movement of the shipping wedge in relation to the staple cartridge, the knife stop extending from the top surface of the proximal portion of the body of the shipping wedge and positioned to obstruct movement of the knife bar of the staple cartridge when the shipping wedge is attached to the staple cartridge, the sled stop member extending from the bottom surface of the proximal portion of the body of the shipping wedge and including an angled stop surface, the sled stop member positioned to obstruct advancement of the actuation sled, the angled stop surface defining an acute angle with the bottom surface of the shipping wedge selected to correspond to an angle defined by the angled distal portion of the actuation sled.

13. The shipping wedge and staple cartridge assembly of claim 12, wherein the elongate fin includes one or more ribs that are dimensioned to increase frictional resistance between the elongate fin and the staple cartridge.

14. The shipping wedge and staple cartridge assembly of claim 12, wherein the shipping wedge includes gripping members that extend transversely of the body of the shipping wedge.

15. The shipping wedge and staple cartridge assembly of claim 12, wherein the at least one tooth includes a tooth positioned on each side of the elongate fin.

16. The shipping wedge and staple cartridge assembly of claim 12, wherein the body of the shipping wedge defines a transverse axis and a longitudinal axis, the body of the shipping wedge having a stepped configuration along the transverse axis.

* * * * *